United States Patent [19]

Mori et al.

[11] Patent Number: 5,534,638
[45] Date of Patent: Jul. 9, 1996

[54] BIS(ETHYLENEDITHIO) TETRATHIAFULVALENE.CYANOMETALATE COMPLEX

[75] Inventors: Hatsumi Mori; Izumi Hirabayashi, both of Aichi; Shoji Tanaka; Takehiko Mori, both of Tokyo; Yusei Maruyama; Hiroo Inokuchi, both of Aichi, all of Japan

[73] Assignee: International Superconductivity Technology Center, Tokyo, Japan

[21] Appl. No.: 429,009

[22] Filed: Apr. 26, 1995

Related U.S. Application Data

[63] Continuation of Ser. No. 50,187, filed as PCT/JP92/01185, Sep. 17, 1992, abandoned.

[30] Foreign Application Priority Data

Sep. 19, 1991 [JP] Japan ..................... 3-268268
Jun. 19, 1992 [JP] Japan ..................... 4-186133

[51] Int. Cl.⁶ .................................... C07D 409/04
[52] U.S. Cl. .................................... 549/3; 505/811
[58] Field of Search .................... 549/3; 505/811

[56] References Cited

U.S. PATENT DOCUMENTS 4,675,415  6/1987  Williams et al. ..................... 549/3

FOREIGN PATENT DOCUMENTS 63-246383  10/1988  Japan .

OTHER PUBLICATIONS

Tanaka et al, CA 111(20):184955e, 1989.
Shibaeva et al, CA 110(20):183443d, 1988.
Kurmoo et al, CA 113(8):67386a, 1990.
Wang et al, CA, 111(18):162961b, 1989.
Keller et al, CA 106(16):130586p, 1986.
CA 113(16):143015w, Stephan et al, 1990.
CA 112(26):242391b, Garrigou–Lagrange et al, 1990.
CA 112(4):28405r, Lobkovskaya et al, 1989.
Ouahab et al, CA 111(22):206623z, 1989.

*Primary Examiner*—Richard L. Raymond
*Assistant Examiner*—Deborah Lambkin
*Attorney, Agent, or Firm*—Evenson, McKeown, Edwards & Lenahan

[57] ABSTRACT

This describes the following five novel organic substances: Bis (ethylenedithio) tetrathiafulvalene (henceforth to be called BEDT-TTF) compounded with cyanometalate anions in what is called Tetracyano Nickel acid Bis (Ethylenedithio) Tetrathiafulvalene salt.hydrate expressed by $(BEDT\text{-}TTF)_4 [Ni(CN)_4] \cdot H_2O$, Tetracyano Platinum acid Bis (Ethylenedithio) Tetrathiafulvalene salt.hydrate that is expressed by $(BEDT\text{-}TTF)_4 [Pt(CN)_4] \cdot H_2O$, Cyanide Palladium Bis (Ethylenedithio) Tetrathiafulvalene salt that is expressed by $(BEDT\text{-}TTF)\text{-}[Pd(CN)_2]$, Tetracyano Palladium acid Bis (Ethylenedithio) Tetrathiafulvalene salt.hydrate that is expressed by $(BEDT\text{-}TFF)_4 [Pd(CN)_4] \cdot H_2O$ and Tetracyano Palladium acid Bis (Ethylenedithio) Tetrathiafulvalene salt that is represented by $(BEDT\text{-}TTF)_4[Pd(CN)_4]$. BEDT-TTF, acting as a common constituent in the crystals of all of the above substances, provides the properties of an insulator, a metal or a superconductor. Anions that construct the framework of BEDT-TTF determine the arrangement of BEDT-TTF and thus the electronic state of the compound. It can be predicted that superconducting phenomena could be discovered in compounds of BEDT-TTF type in which there are compounded cyanometalate anions that have the tendency to form large frameworks so that the effective volume is large as in the case of the novel substances of the present invention.

2 Claims, 22 Drawing Sheets

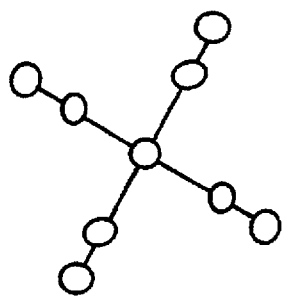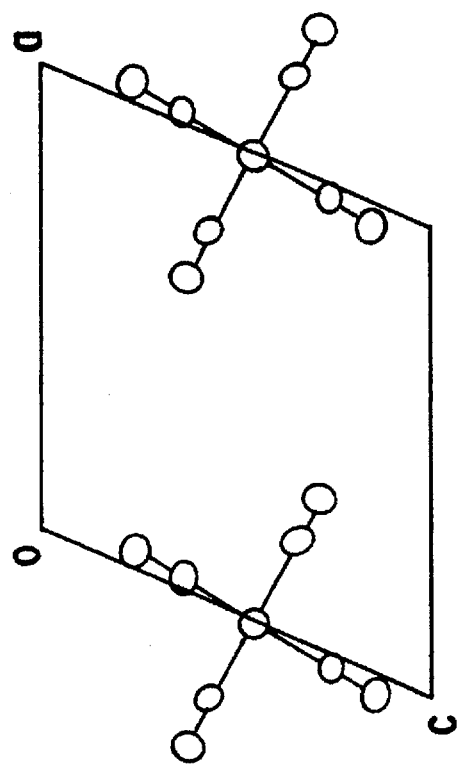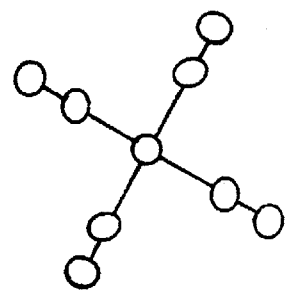
FIG. 10

|  | $(BEDT-TTF)_4-$ $[Ni(CN)_4] \cdot H_2O$ | $(BEDT-TTF)_4-$ $[Pt(CN)_4] \cdot H_2O$ | $(BEDT-TTF)-$ $[Pd(CN)_2]$ | $(BEDT-TTF)_4-$ $[Pd(CN)_4] \cdot H_2O$ | $(BEDT-TTF)_4-$ $[Pd(CN)_4]$ |
|---|---|---|---|---|---|
| COLOR | BLACK | BLACK | BLACK | BLACK | BLACK |
| SHAPE | PLATE | PLATE | PLATE | PLATE | PLATE |
| Electrical conductivity (at room temperature) | | | | | |
| $(Scm^{-1})$ | 70–110 | 130–280 | 7.0 | – | 100 |
| Metal to insulator transition temperature | $T_{MI}=100K$ | $T_{MI}=120K$ | semi-conductor | $T_{MI}=100K$ | $T_{MI}=120K$ |
| Molecular weight | 1719.4 | 1855.8 | – | 1767.2 | 1749.2 |
| CRYSTAL SYSTEM | triclinic | triclinic | monoclinic | triclinic | triclinic |
| SPACE SYSTEM | $P\bar{1}$ | $P\bar{1}$ | – | $P\bar{1}$ | $P\bar{1}$ |
| $a$/ | 11.493 | 11.514 | 34.913 | 11.529 | 10.997 |
| $b$ | 16.693 | 16.704 | 13.470 | 16.685 | 16.546 |
| $c$ | 9.543 | 9.563 | 15.010 | 9.562 | 9.735 |
| $\alpha/°$ | 91.28 | 91.22 | – | 91.32 | 98.15 |
| $\beta$ | 112.47 | 112.30 | 108.50 | 112.29 | 115.15 |
| $\gamma$ | 75.57 | 75.48 | – | 75.63 | 95.85 |
| $V/^3$ | 1632.9 | 1641.6 | 6694.3 | 1643.3 | 1561.0 |
| $Z$ | 1 | 1 | – | 1 | 1 |
| DENSITY $(g/cm^3)$ | 1.75 | 1.88 | – | 1.79 | 1.86 |
| Reflected data points | 5243 | 6037 | – | 4825 | 5038 |
| R VALUE | 0.069 | 0.041 | – | 0.072 | 0.061 |

FIG.11

(a) $(BEDT-TTF)_4 Pd(CN)_4 H_2O$ (b) $(BEDT-TTF)_4 Pd(CN)_4$

BIS(ETHYLENEDITHIO) TETRATHIAFULVALENE.CYANOMETALATE COMPLEX

This application is a continuation of application Ser. No. 08/050,187, filed as PCT/JP92/01185, Sep. 17, 1992, abandoned.

TECHNICAL FIELD

This invention relates to the organic compound of bis (ethylenedithio) tetrathiafulvalene (henceforth called BEDT-TTF) and especially relates to a novel substance that forms an insulator, a metal and a superconductor with BEDT-TFF participating as the common constituent. It also relates to a new substance of BEDT-TTF.cyanometalate complex, where cyanometalate anions are compounded with BEDT-TTF that has a high potential for forming structures with superconducting states.

BACKGROUND

Present day research and development activities on superconductors have given much attention to the fact that there are peculiarities in the behavior of a superconductor with respect to the electrical resistance and magnetization. These researches, starting from metallic superconductors of alloys and chemical compounds, have expanded its limits to include organic compounds as well. As at present, them are about 50 kinds of organic compounds that show superconducting transition, their critical temperatures being at the most about 45K.

Even among the organic compounds, the compound BEDT-TFF attracts much attention for the reason that BEDT-TTF can act as a common constituent in preparing various complexes of insulators, metals and superconductors. The structural formula for BEDT-TTF is shown in FIG. 1.

A BEDT-TTF compound of the form $(BEDT-TTF)_2X$ shows several superconducting phenomena, and the critical temperatures for such phenomena have a positive correlation to the volume (or rather the effective volume) occupied by the conduction layers that contain BEDT-TFF. In order to increase the effective volume, now it has come to the stage of searching for anions, which constitute a large frame work for conduction layers.

Research and development efforts on preparation and observation of cyanometalates and thiocyanometalate compounds of BEDT-TTF have produced substances such as k-$(BEDT-TTF)_2[Cu(NCS)_2]$, $(BEDT-TTF)_2$ $[NH_4Hg(SCN)_4]$, k-$(BEDT-TTF)_2[Ag(CN)_2]H_2O$, which are known to show superconductivity.

The molecular arrangement of BEDT-TFF is determined by the framework of anions $X^-$, which determine the electronic state of the compounds. These anions that set up the framework for BEDT-TFF are the key to controlling the electronic state, or in other words, they are the key to the discovery of superconductors. It can be predicted that there exist substances that are superconducting and that are the compounds of cyanometalate or thiocyanometalate anions with BEDT-TFF, which have the tendency to form a cluster or polymer so that the effective volumes are large.

Similar to thiocyanometalate anions that are contained in BEDT-TTF complexes that show superconducting transition, the cyanate anions have the nature of forming coordination bond with transition metals or forming hydrogen bonds with molecules of water. In BEDT-TTF compounds, there are instances of the BEDT-TTF arrangement being controlled by pseudo-halogenate anions, which form anion clusters or polymers. The electronic state attained as a result of this BEDT-TFF arrangement provides several superconductors.

The present invention has the objective of obtaining a novel BEDT-TTF type organic material, because it is considered that BEDT-TTF is an effective multi-purpose material that develops superconductivity.

DISCLOSURE OF THE INVENTION

The crystal structure of the substance of the present invention is illustrated by giving examples of a few types of substances. FIG. 2 is the crystal structure of Tetracyano platinum acid bis (ethylenedithio) tetrathiafulvalene salt.hydrate represented by $(BEDT-TTF)_4 [Pt(CN)_4].H_2O$. FIG. 3 is the crystal structure of tetracyano palladium acid bis (ethylenedithio) tetrathiafulvalene salt.hydrate represented by $(BEDT-TTF)_4 [Pd(CN)_4].H_2O$. FIG. 4 is the crystal structure of palladium acid bis (ethylenedithio) tetrathiafulvalene salt represented by $(BEDT-TFF)_4 Pd(CN)_4$.

It can be understood from these figures that conduction and insulating layers are stacked alternately in the direction of b axis: in FIG. 2, the conduction layer is BEDT-TFF and the insulating layer is anions containing $[Pt(CN)_4]^{2-}$ and $H_2O$; in FIG. 3, the conduction layer is BEDT-TTF and the insulating layer is anions containing $[Pd(CN)_4]^{2-}$ and $H_2O$; in FIG. 4, the conduction layer is BEDT-TFF and the insulating layer is anions containing $[Pd(CN)_4]^{2-}$.

FIGS. 5, 6 and 7 show the molecular arrangements of BEDT-TTF, which is the common constituent in the crystal structures of FIGS. 2, 3 and 4. The interactions between BEDT-TTF molecules in FIGS. 5, 6 and 7 act not only in the direction in which the molecules stack, but also in two other directions lateral to the stacking direction. Though in FIGS. 5, 6 and 7, the molecular arrangements look almost alike, the angle between the anion and the doner planes slightly differes: for instance it is 68° in FIG. 6 and 78° in FIG. 7.

FIGS. 8, 9 and 10 are those dram for the anion arrangement of the crystal structures in FIGS. 2, 3 and 4, respectively. As shown in FIG. 8, $[Pt(CN)_4]^{2-}$ has the planar square shape and $[Pt(CN)_4]^{2-}$ is located on the inversion center. On the other hand, $H_2O$ has a disorder in its spatial packing and the oxygen is located at two sites 0.6Å from the center of symmetry each with an existence probability of 0.5. $[Pt(CN)_4]^{2-}$ and $H_2O$ forms the structure for the spatial packing of BEDT-TFF arrays, the arrays being formed by maintaining the symmetry with an anomalous anion polymer.

As in FIG. 9, $[Pd(CN)_4]^{2-}$ forms the planar square structure and it is located on the inversion center. As for $H_2O$, similar to Platinum salts, spatial arrangement of $H_2O$ is disordered and oxygen molecules are located at two sites 0.6Å from the center of symmetry each with an existence probability of 0.5. CN constitutes with hydrogen molecules of water a hydrogen bond of the type H—O—H . . . N—C to form the cluster, $([Pd(CN)_4] H_2O)^{2-}$. Even in the case of FIG. 10, $[Pd(CN)_4]^{2-}$ forms the planar square shape and is arranged in the anion layer.

Substances having a structure such as above undergoes on cooling at normal pressure a transition from metal to insulator. On cooling under pressure, they will show superconducting transition. The substance of the present invention is a novel organic material, and is expected to find many applications that make use of these properties.

BRIEF DESCRIPTION OF THE DRAWINGS

FIG. 10 is the diagram showing the crystal structure of the organic substance of the present invention, $(BEDT-TTF)4 Pd(CN)_4$.

FIG. 11 is a table showing the analytical results of the organic substance of the present invention.

THE MOST APPROPRIATE COMPOUND STRUCTURE FOR PUTTING THE PRESENT INVENTION IN OPERATION

FIG. 11 shows the physical and chemical properties investigated by a single crystal of the following organic compounds of the present invention: (1) $(BEDT-TTF)_4 [Pt(CN)_4].H_2O$, (2) $(BEDT-TFF)_4 Ni(CN)_4.H_2O$, (3) $(BEDT-TTF)-[Pd(CN)_2]$, (4) $(BEDT-TTF)_4 [Pd(CN)_4].H_2O$ and $(BEDT-TFF)_4 [Pd(CN)_4]$. Atomic coordinates in the chart were obtained by a structural analysis in which Patterson method was used and the convergence was made by the Block-diagonal least-square method. Electrical conductivity was measured in the standard four-wire configuration in which a 100 Hz alternating current was passed in a gold wire of 25 mm diameter that was pasted to the single crystal. Each of the single crystal was prepared by a standard electrochemical method where a low-level current of 0.5 μA is passed through a reasonably electrolytic mixture in 1,1,2-trichloroethane and 10% enthanol in volume.

The present invention is described below based on the physical and chemical properties of the organic compounds shown in FIG. 11.

(1) $(BEDT-TTF)_4 [Pt(CN)_4.H_2O$

The electrochemical oxidation of BEDT-TTF was carried out by using $BaPt(CN)_4$, KCN and 18-crown-6 ether as the electrolytes to make single crystals under the above conditions. This effort produced single crystals which have plate-like shapes and which are black in color. Measurements with an Electron-probe X-ray micro-analyzer (EPMA) confirmed that Pt is contained in the single crystal. Analysis showed that the composition of the crystal is $(BEDT-TFF)_4 [Pt(CN)_4].H_2O$ and that the crystal system is triclinic and the space group belongs to $P\bar{1}$. Measurements of the electrical conductivity showed that the electrical conductivity is 130 to 280 $Scm^{-1}$ at room temperature. This conductivity is larger compared to other metallic complex salts of BEDT-TTF.

Figure 1:
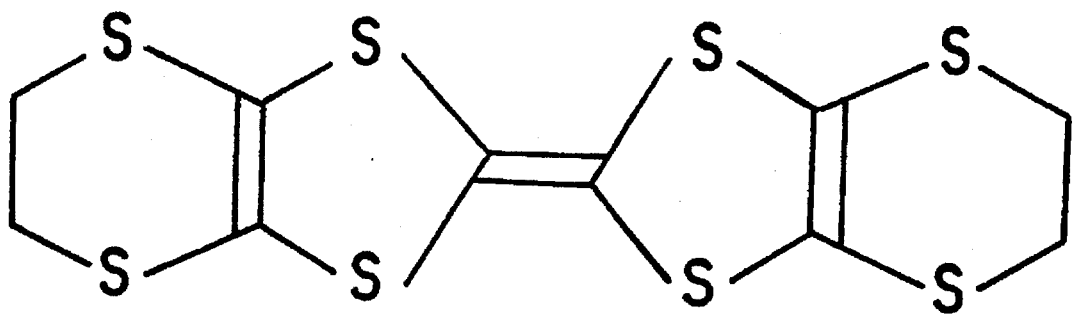
FIG. 1 is a diagram showing the molecular structure of BEDT-TTF.
Figure 2:
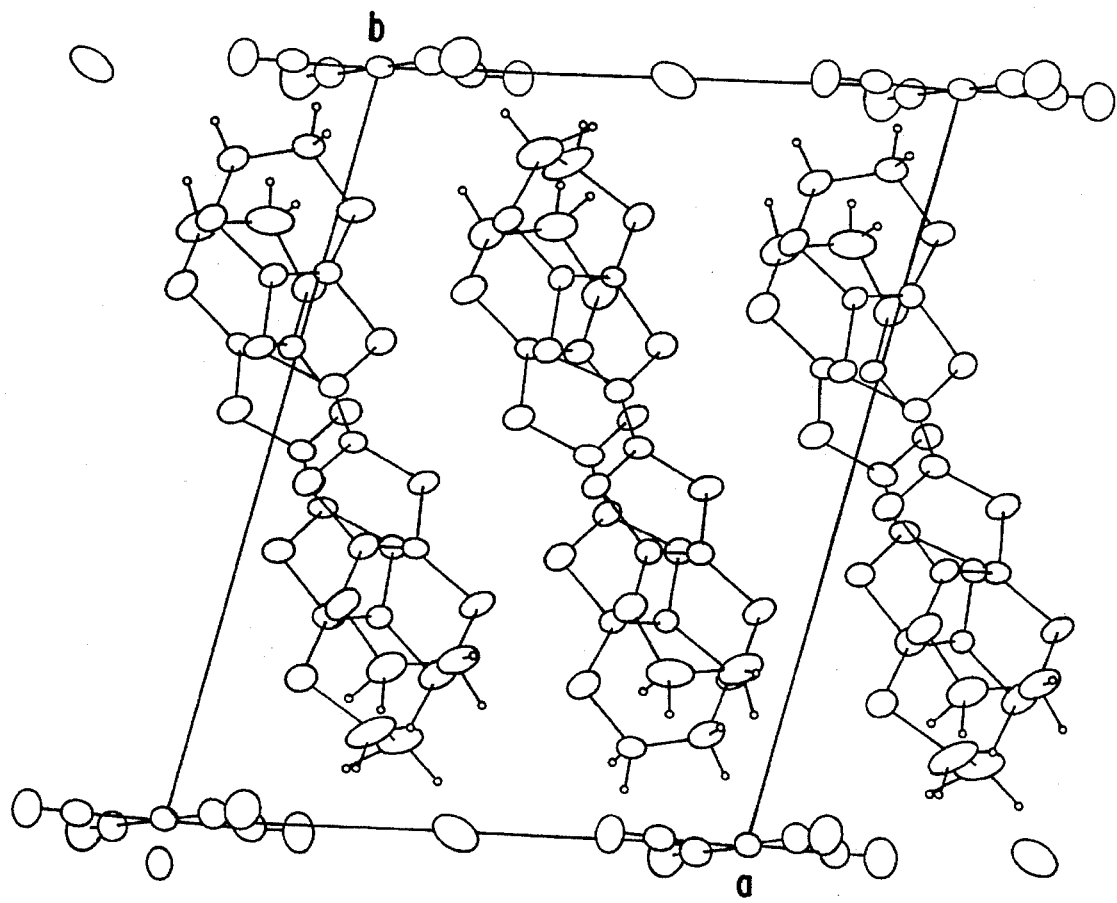
FIG. 2 is the diagram showing the crystal structure of the organic substance of the present invention, $(BEDT-TTF)_4 [Pt(CN)_4].H_2O$.
Figure 3:
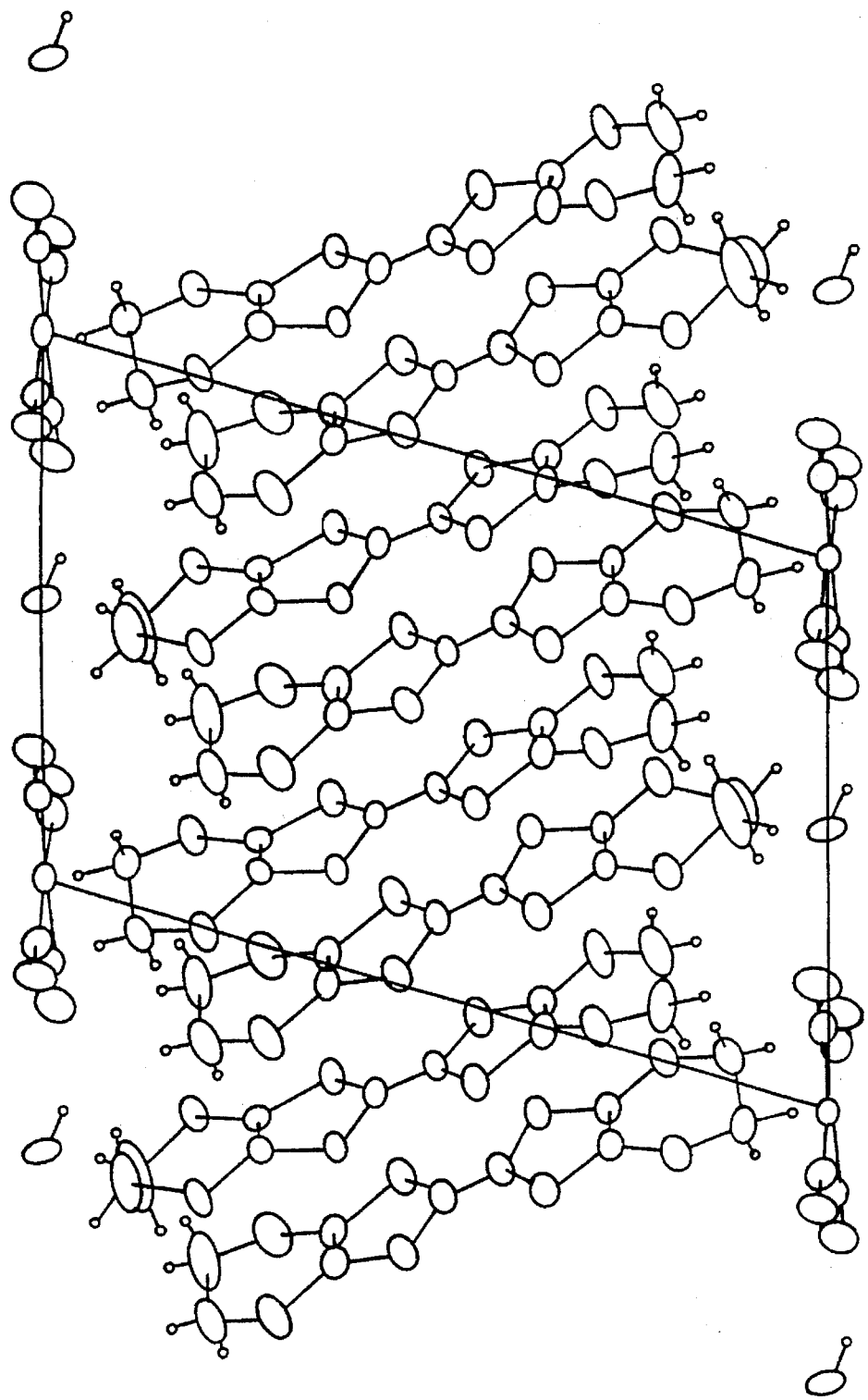
FIG. 3 is the diagram showing the crystal structure of the organic substance of the present invention, $(BEDT-TTF)_4 [Pd(CN)_4].H_2O$.
Figure 4:
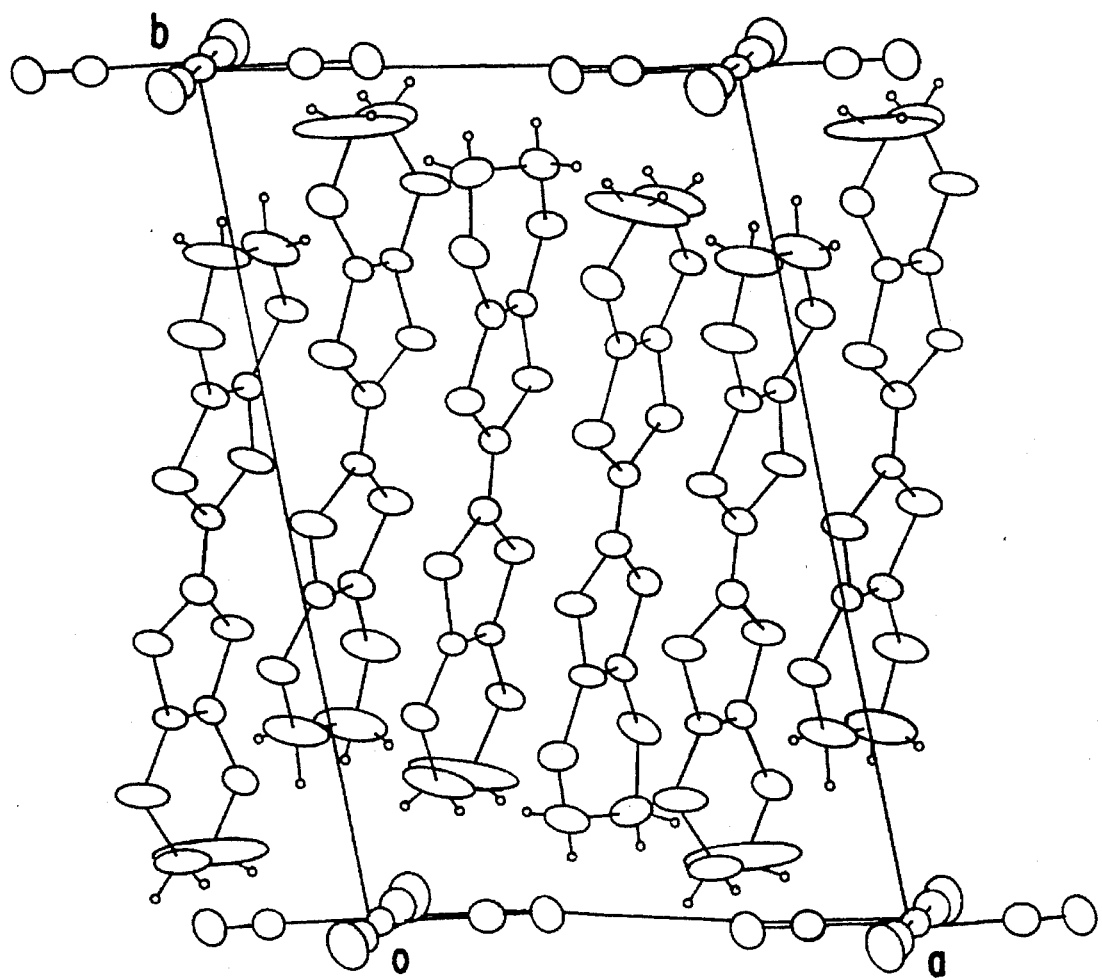
FIG. 4 is the diagram showing the crystal structure of the organic substance of the present invention, $(BEDT-TTF)_4 Pd(CN)_4$.
Figure 5:
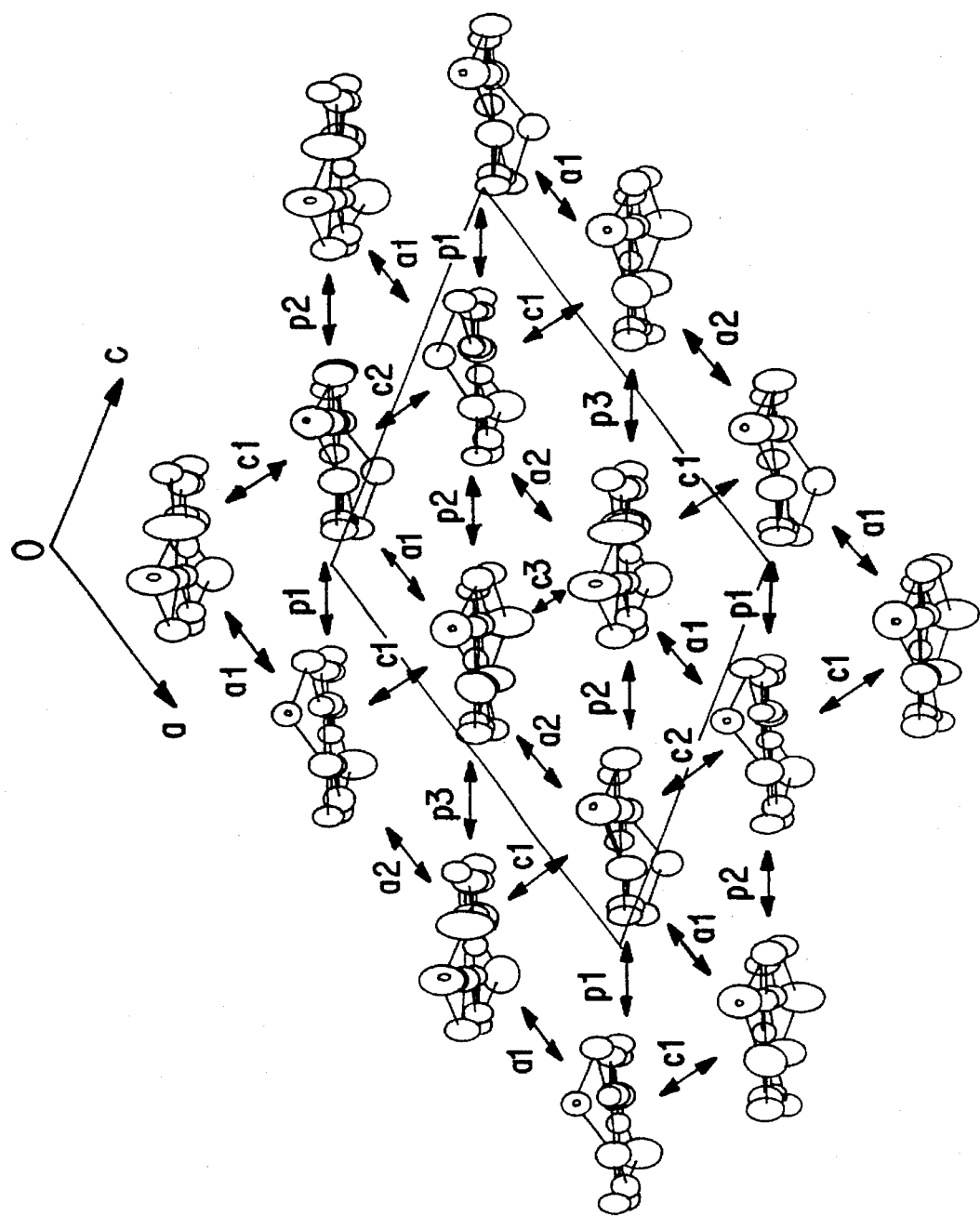
FIG. 5 is the diagram showing the crystal structure of the organic substance of the present invention, $(BEDT-TFF)_4 [Pt(CN)_4].H_2O$.
Figure 6:
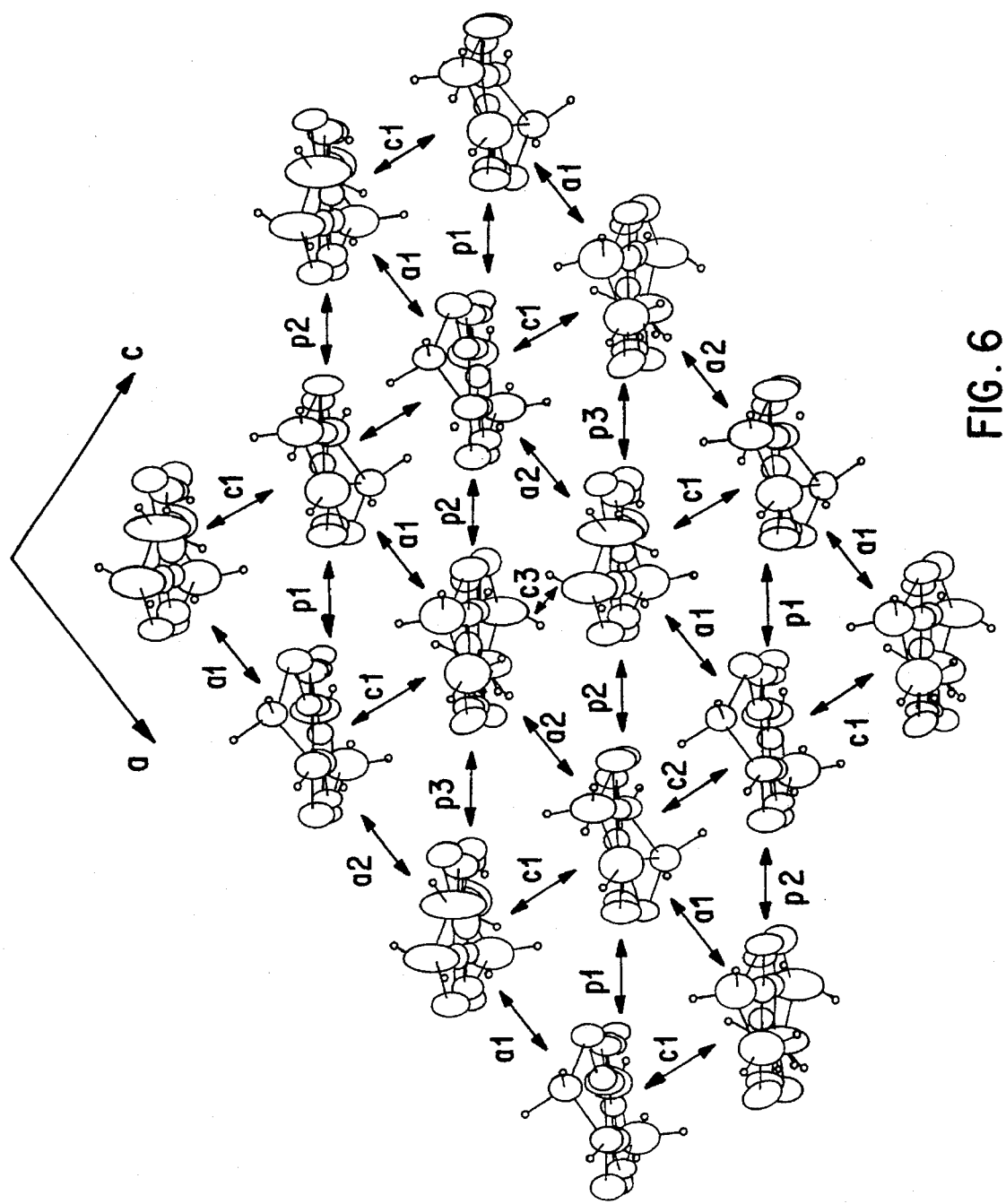
FIG. 6 is the diagram showing the crystal structure of the organic substance of the present invention, $(BEDT-TFF)_4 [Pd(CN)_4].H_2O$.
Figure 7:
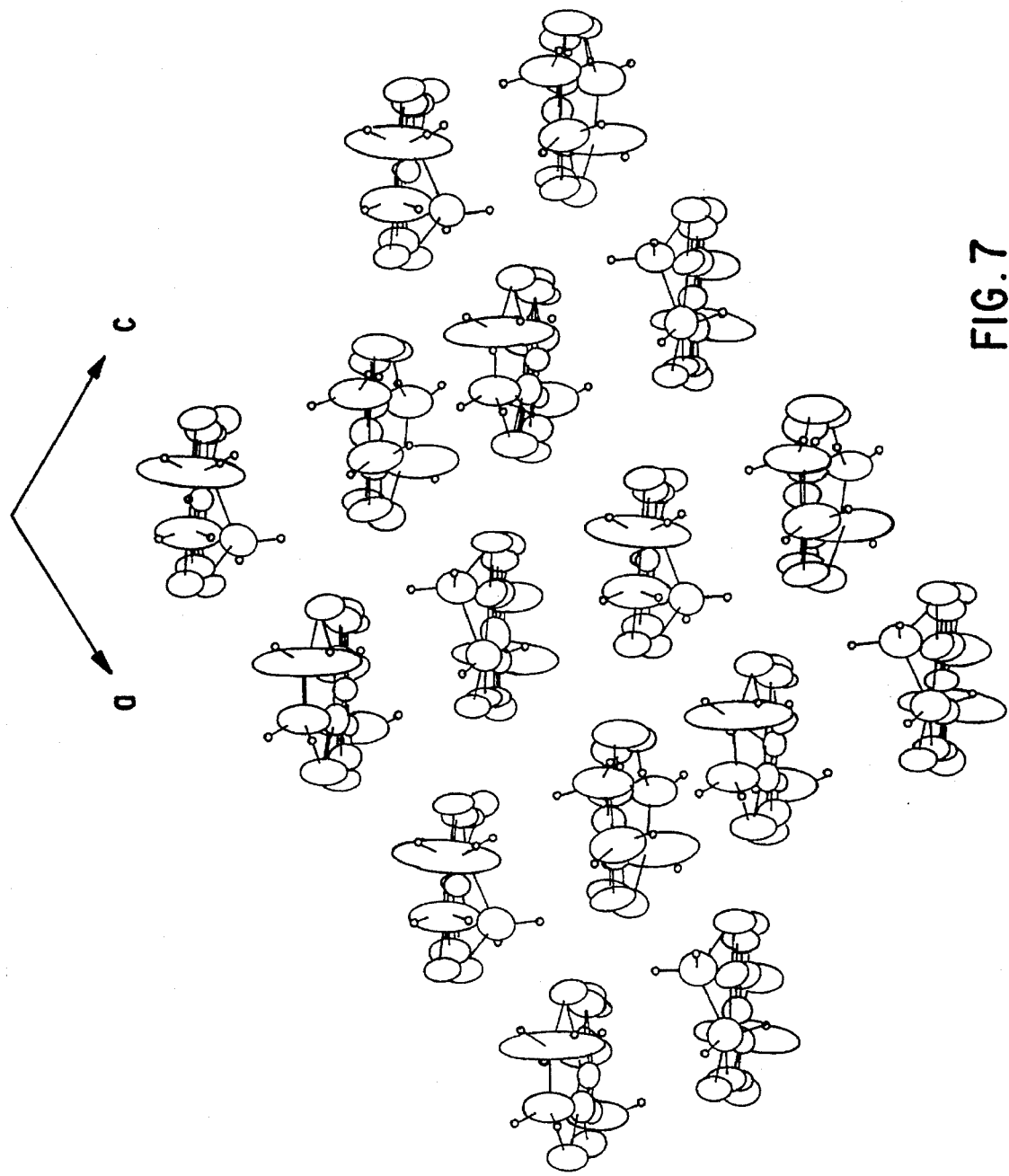
FIG. 7 is the diagram showing the crystal structure of the organic substance of the present invention, $(BEDT-TTF)_4 Pd(CN)_4$.
Figure 8:
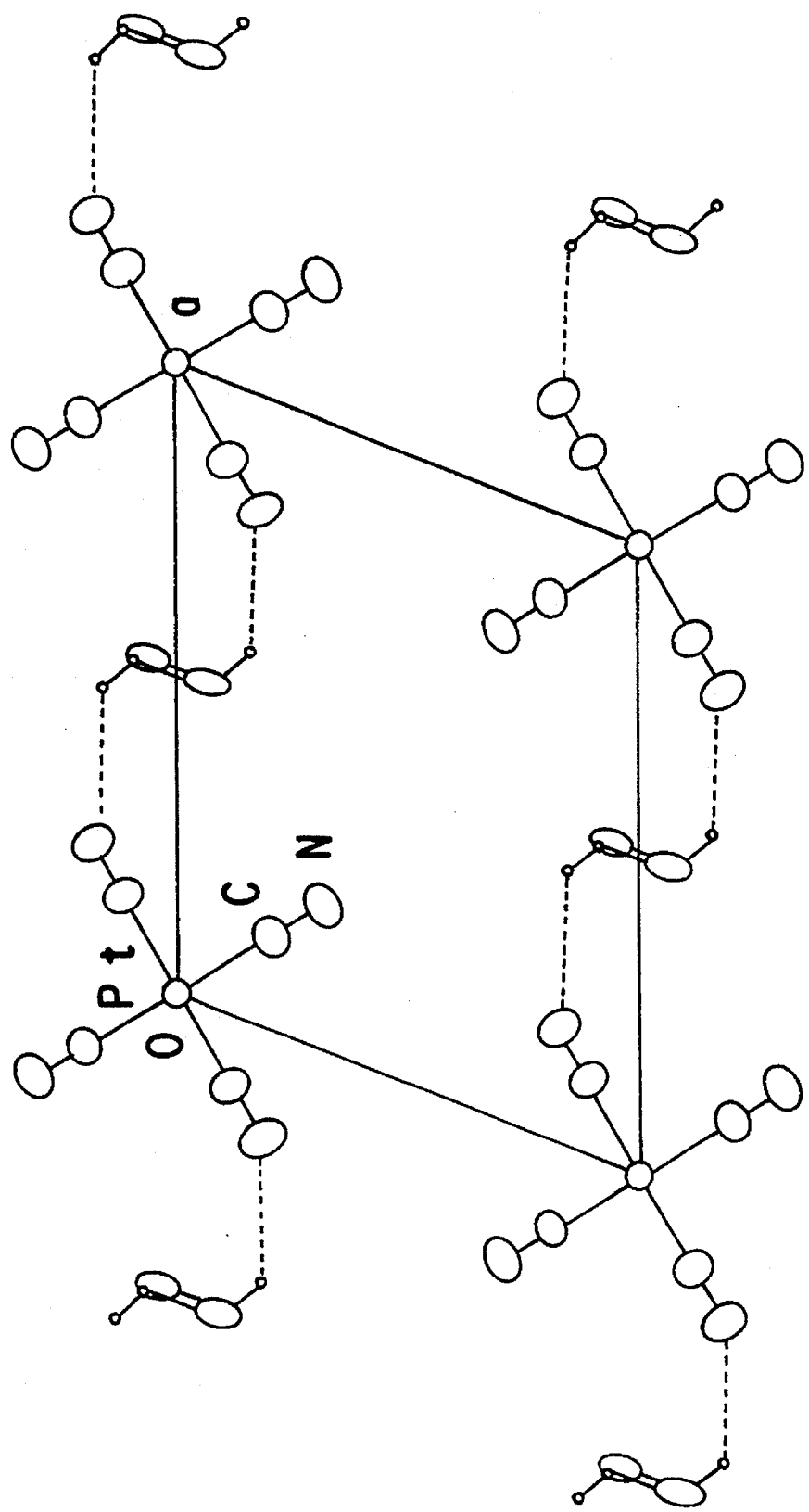
FIG. 8 is the diagram showing the crystal structure of the organic substance of the present invention, $(BEDT-TTF)_4 [Pt(CN)_4].H_2O$.
Figure 9:
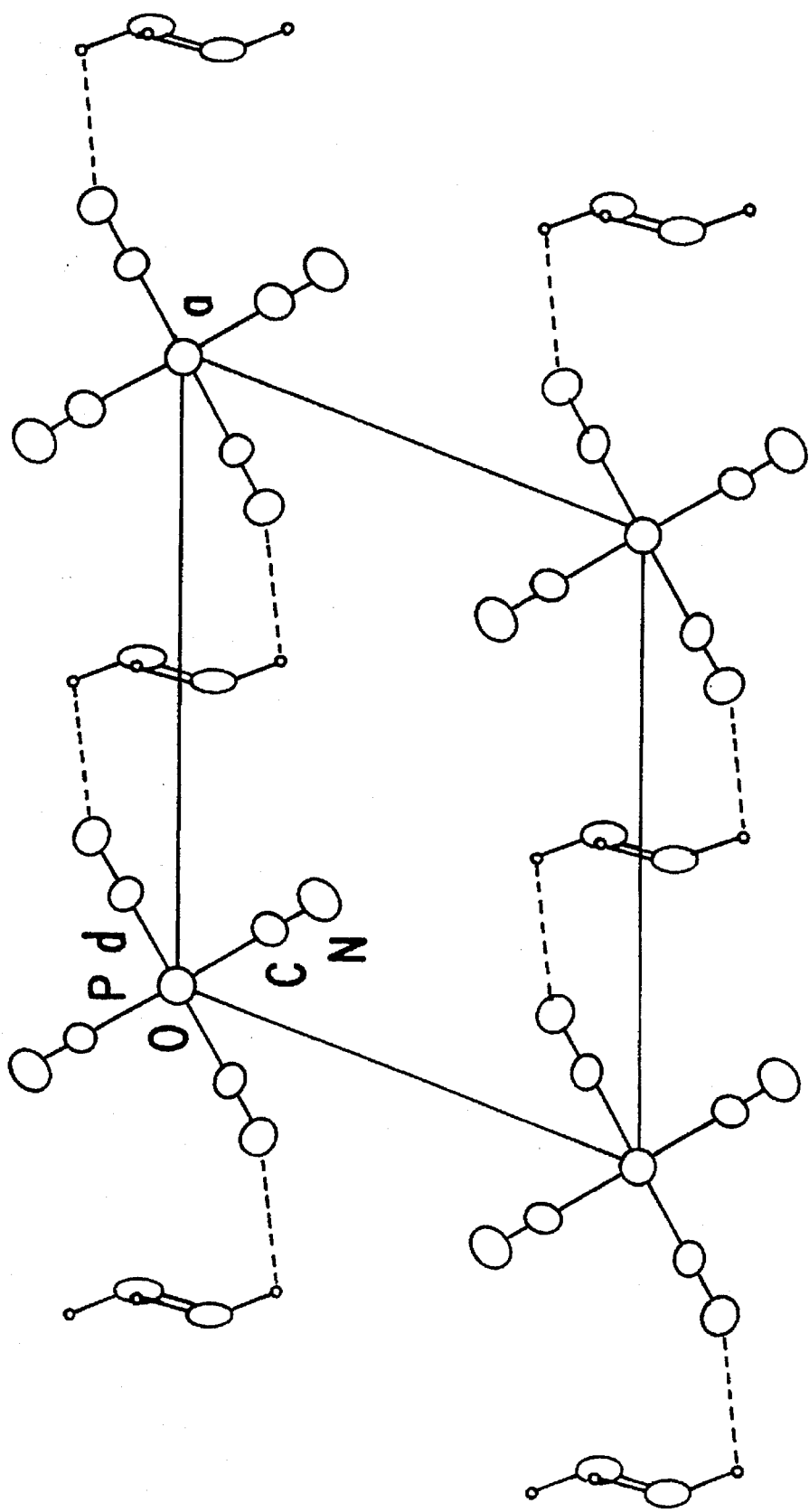
FIG. 9 is the diagram showing the crystal structure of the organic substance of the present invention, $(BEDT-TFF)_4 [Pd(CN)_4].H_2O$.

As for the molecular arrangements of anions and water molecules in the present substance shown in FIG. 8, it can be seen that they form an anion cluster strongly bonded by hydrogen bonds.

Figure 12:
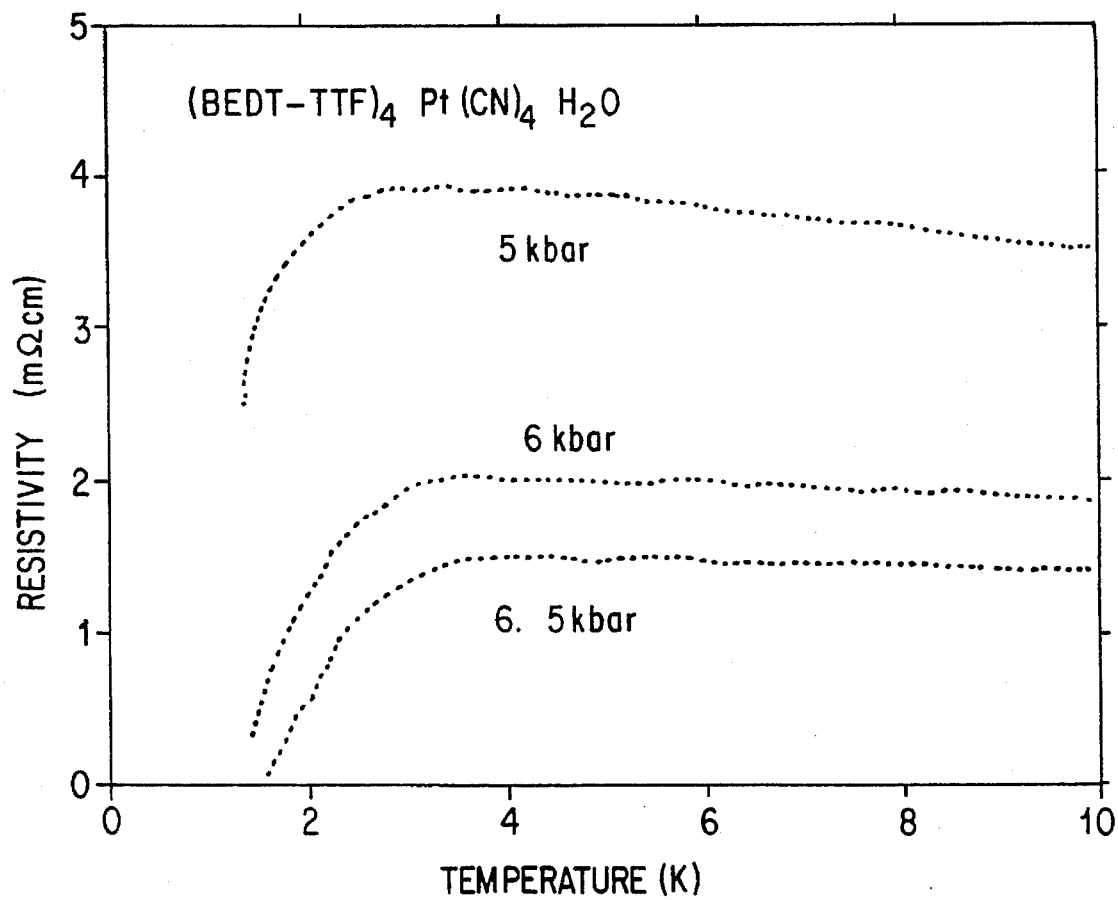
FIG. 12 is the plot showing the temperature dependence of the electrical resistance under pressure of the organic substance of the present invention, $(BEDT-TTF)_4 Pt(CN)_4.H_2O$.
Figure 13:
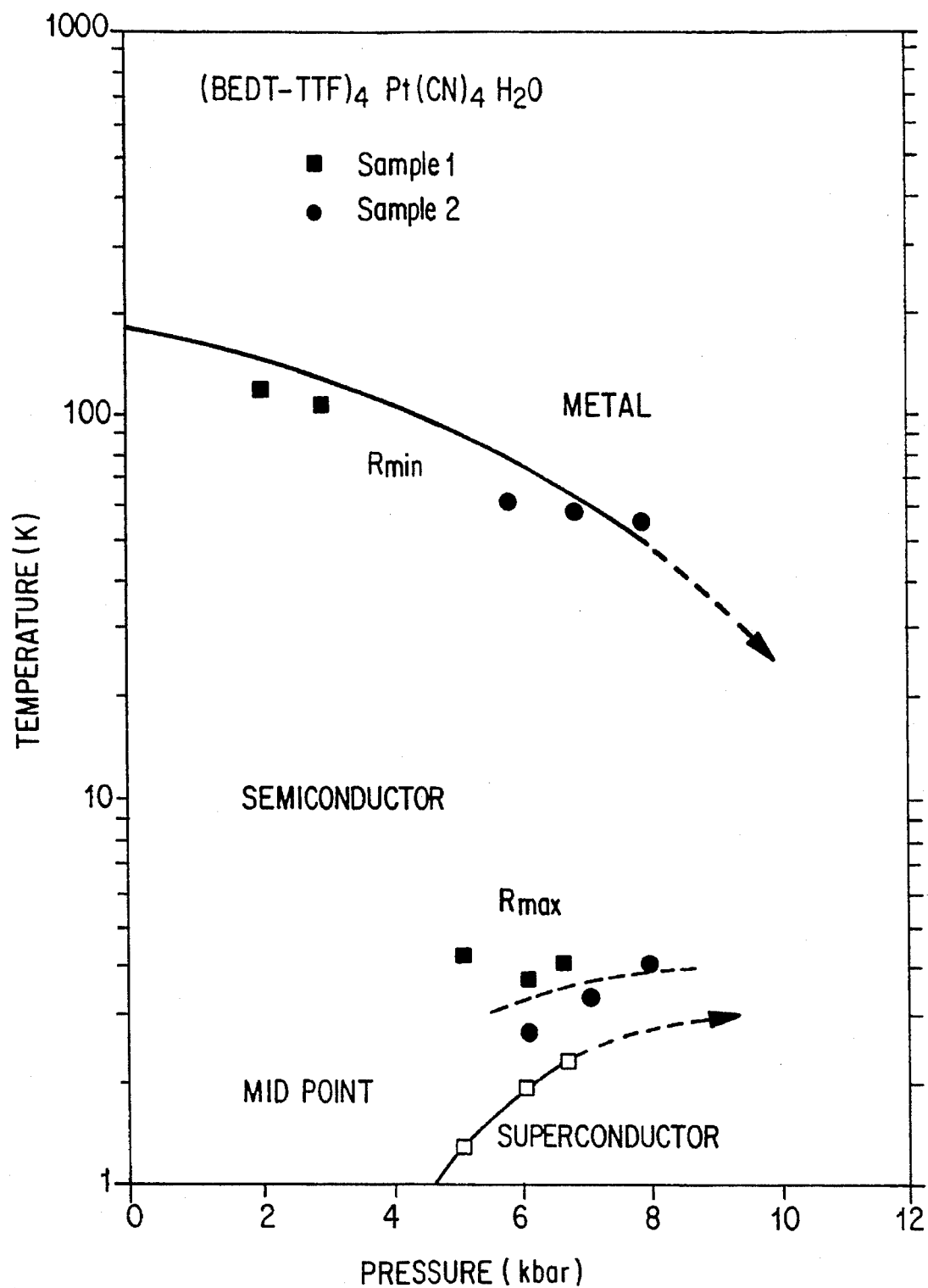
FIG. 13 is a phase diagram of behavior of the electrical resistance of the present invention, $(BEDT-TTF)_4 [Pt(CN)_4].H_2O$.

FIG. 12 shows the graph of the temperature dependence of electrical resistance of $(BEDT-TFF)_4 [Pt(CN)_4].H_2O$ under pressure. Measurements on temperature dependence of the electrical resistance at the pressures, 5 kbar, 6 kbar and 6.5 kbar showed that the resistance rapidly decreased at 2K in each case, and that it was possible to observe superconducting state by observing the elimination of the resistive drop in a magnetic field. FIG. 13 shows these results by way of a phase diagram. When being cooled under normal pressure, transition from metal to insulator occured around 120K, while under pressurized state at 6.5 kbar, cooling produced a superconducting state with a critical temperature of 2K.

(2) $(BEDT-TFF)_4 [Ni(CN)_4].H_2O$

The electrochemical oxidation of BEDT-TTF was carried out by using $K_2Ni(CN)_2$, KCN and 18-crown-6 ether as electrolytes to make single crystals under the above mentioned conditions. This effort produced single crystals which have platelike shapes and are black in color. Measurements with an Electron-probe X-ray micro-analyzer (EPMA) confirmed that Ni is contained in the single crystal. Analysis showed that the composition of the crystal is (BEDT-TFF)$_4$[Ni(CN)$_4$].H$_2$O and that the crystal system is triclinic and the space group belongs to P$\bar{1}$. This substance is crystallographically identical to (BEDT-TFF)$_4$[Pt(CN)$_4$].H$_2$O of (1). Measurements of the electrical conductivity showed that the electrical conductivity is 70 to 110 Scm$^{-1}$ at room temperature and that conductivity is somewhat smaller compared to (BEDT-TTF)$_4$[Pt(CN)$_4$].H$_2$O.

Figure 14:
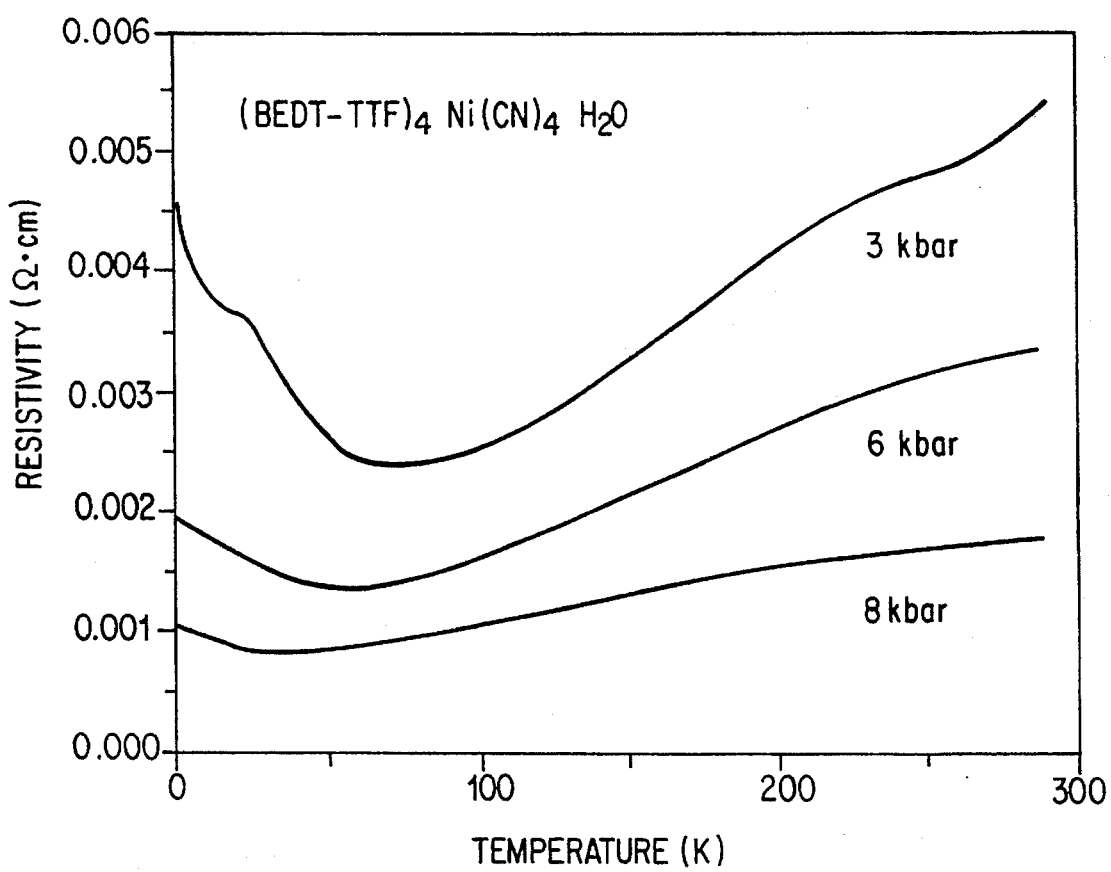
FIG. 14 is the plot showing the temperature dependence of the electrical resistance under pressure of the organic substance of the present invention, $(BEDT-TTF)_4 Ni(CN)_4.H_2O$.

FIG. 14 shows the graph of the temperature dependence under pressure of electrical resistance of the present substance. If cooled below 100K, transition from metal to insulator occurs. However, even at 1.5K, the degree of resistance increase is only about one order of magnitude compared to the resistance at room temperature. Further pressurizing up to 8 kbar could somewhat suppress the metal-insulator transition, yet superconducting phenomenon could not be observed.

(3) (BEDT-TTF)-[Pd(CN)$_2$]

Figure 15:
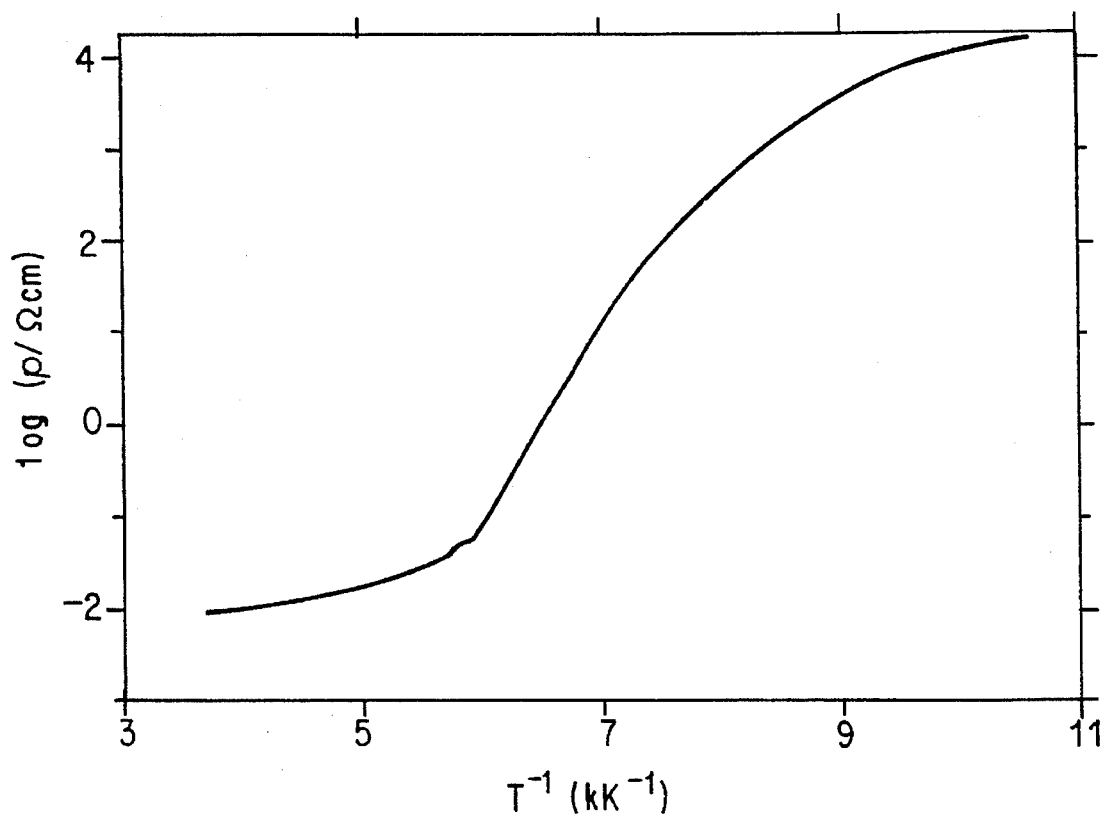
FIG. 15 is the plot showing the temperature dependence of the electrical resistance at normal pressure of the organic substance of the present invention, $(BEDT-TFF)-[Pd(CN)_2]$.

Electrochemical oxidation of BEDT-TTF was done by using Pd(CN)$_2$, KCN and 18-crown-6 ether as electrolytes to make single crystals under the above conditions. This effort produced single crystals which have platelike shapes and which are black in color. Analysis showed that the composition of the crystal is (BEDT-TTF)-[Pd(CN)$_2$] and that the crystals belong to the monoclinic system. Crystal structure is considerably different from the structures of (1) and (2) above, and also the physical properties are significantly different. Measurements of electrical conductivity showed that the crystal is a semiconductor having an electrical conductivity of about 70 Scm$^{-1}$ at room temperature. As the next step, temperature dependence of the electrical conductivity under pressurized state was examined and the results of this examination are shown in FIG. 15.

Although the crystal shows a high conductivity at room temperature, it shows a semiconductor-like resistance increases when being cooled.

(4) (BEDT-TFF)$_4$[Pd(CN)$_4$].H$_2$O and (BEDT-TTF)$_4$[Pd(CN)$_4$]

Electrochemical oxidation of BEDT-TTF was done by using Pd(CN)$_2$, KCN and 18-crown-6 ether as electrolytes to make single crystals under the above mentioned conditions. (BEDT-TTF)$_4$[Pd(CN)$_4$].H$_2$O was obtained when 10% ethanol was added to the solution, and on the other hand. (BEDT-TTF)$_4$[Pd(CN)$_4$] was obtained when ethanol was not added. The crystal systems were both triclinic and the space group belonged to P$\bar{1}$.

Figure 16B:
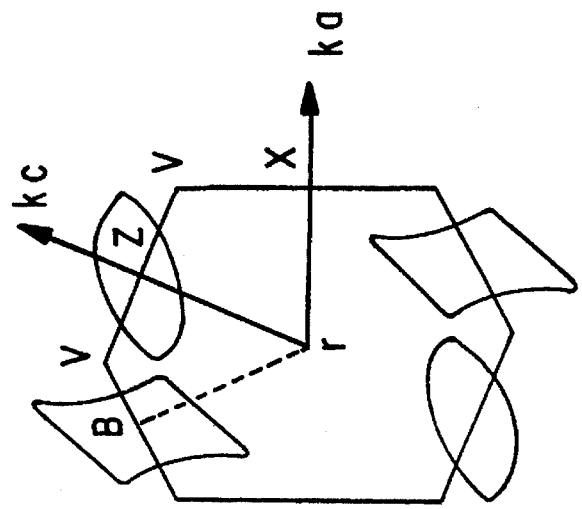
FIG. 16 shows the band structure of the organic substance of the present invention, $(BEDT-TFF)_4 [Pd(CN)_4].H_2O$.
Figure 16:
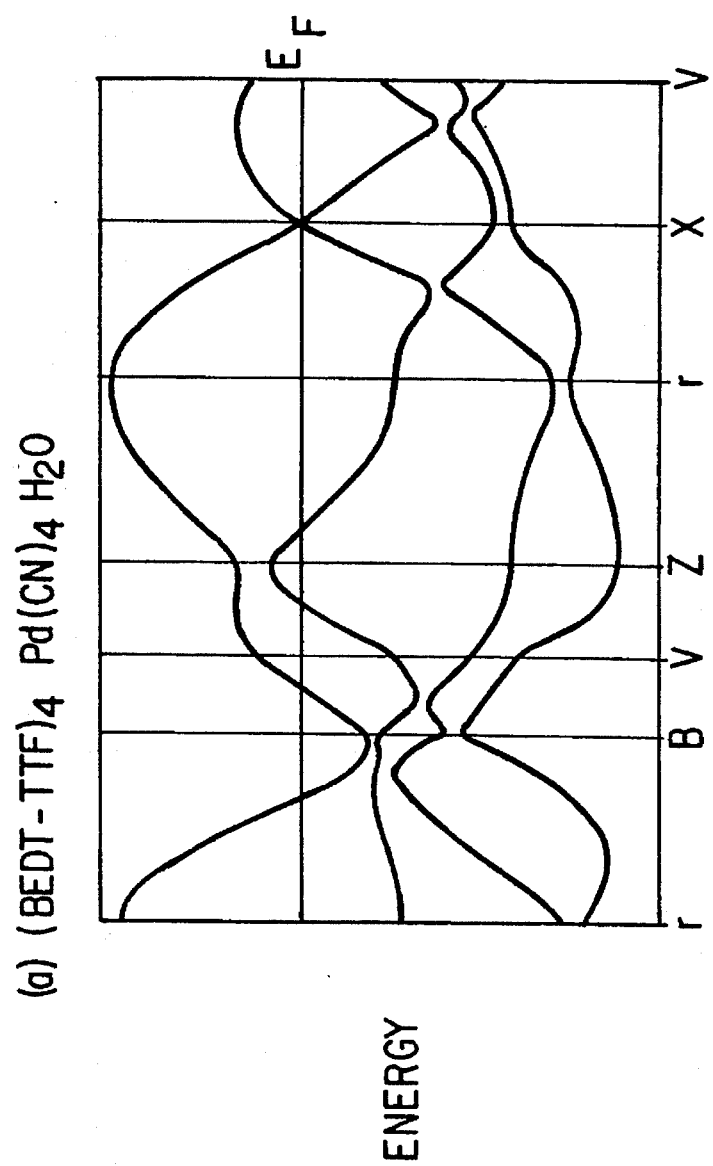
Figure 17A:
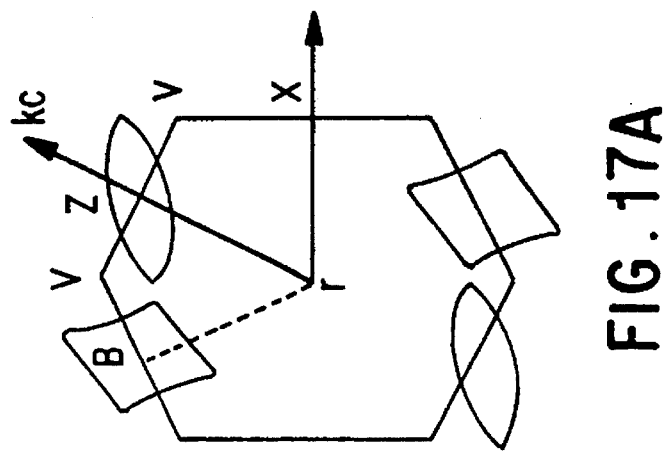
FIG. 17 shows the band structure of the organic substance of the present invention, $(BEDT-TTF)_4 [Pd(CN)_4]$.
Figure 17:
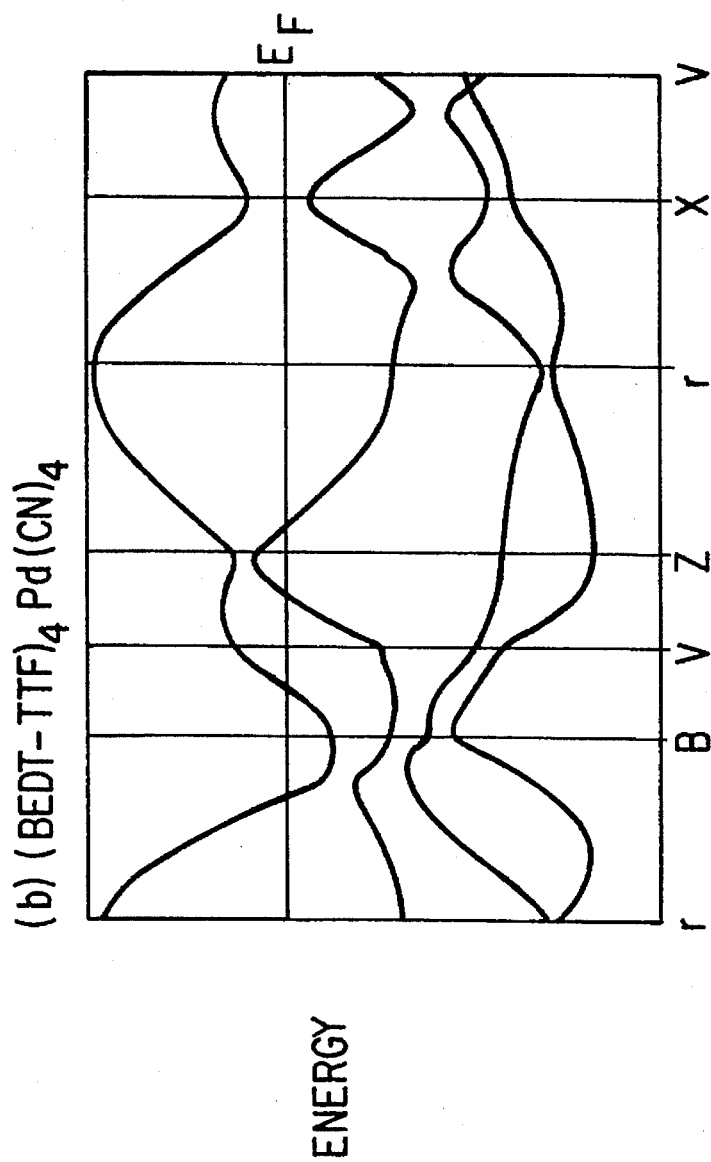

FIGS. 16 and 17 show respectively the band structures of (BEDT-TTF)$_4$[Pd(CN)$_4$].H$_2$O and (BEDT-TTF)$_4$[Pd(CN)$_4$]. As shown in FIG. 16 and 17, both band structures are semimetallic, and their Fermi surfaces have become a pocket of both electrons and holes.

Figure 18:
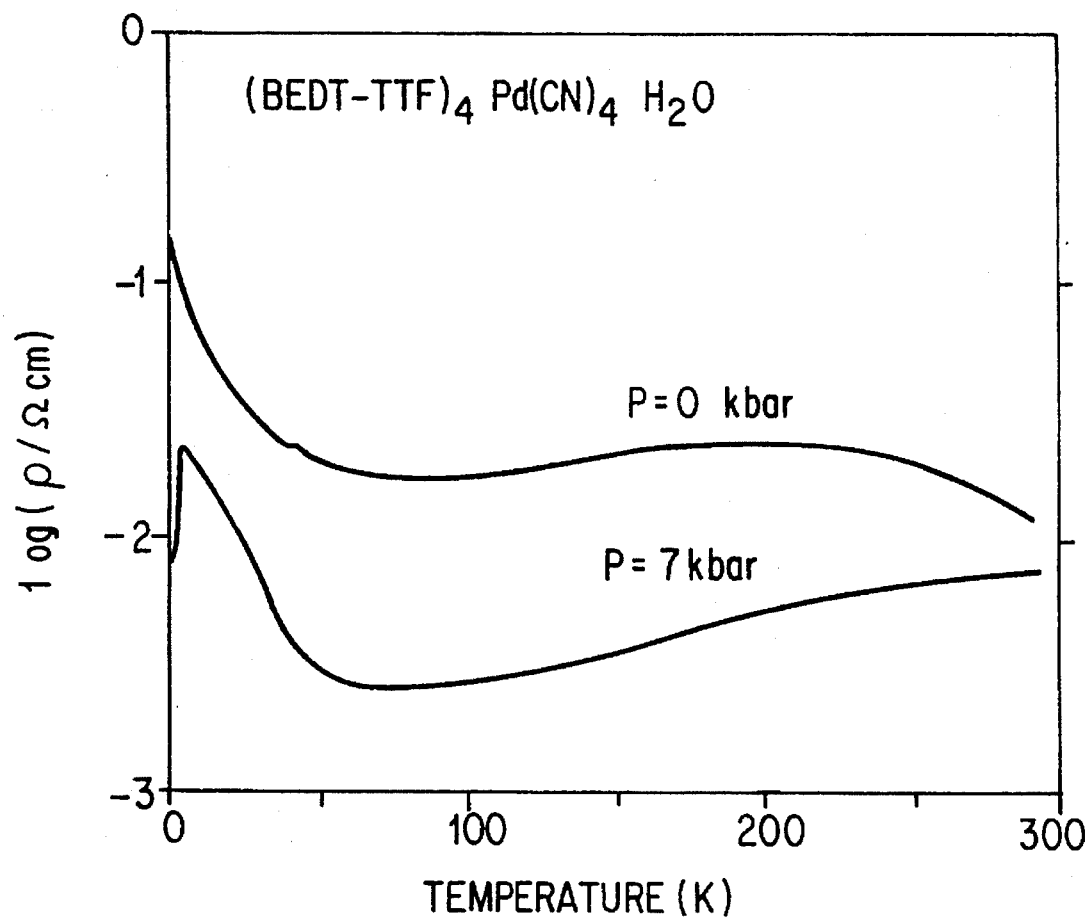
FIG. 18 is the plot showing the temperature dependence of the electrical resistance under pressure of the organic substance of the present invention, $(BEDT-TTF)_4[Pd(CN)_4].H_2O$.
Figure 19:
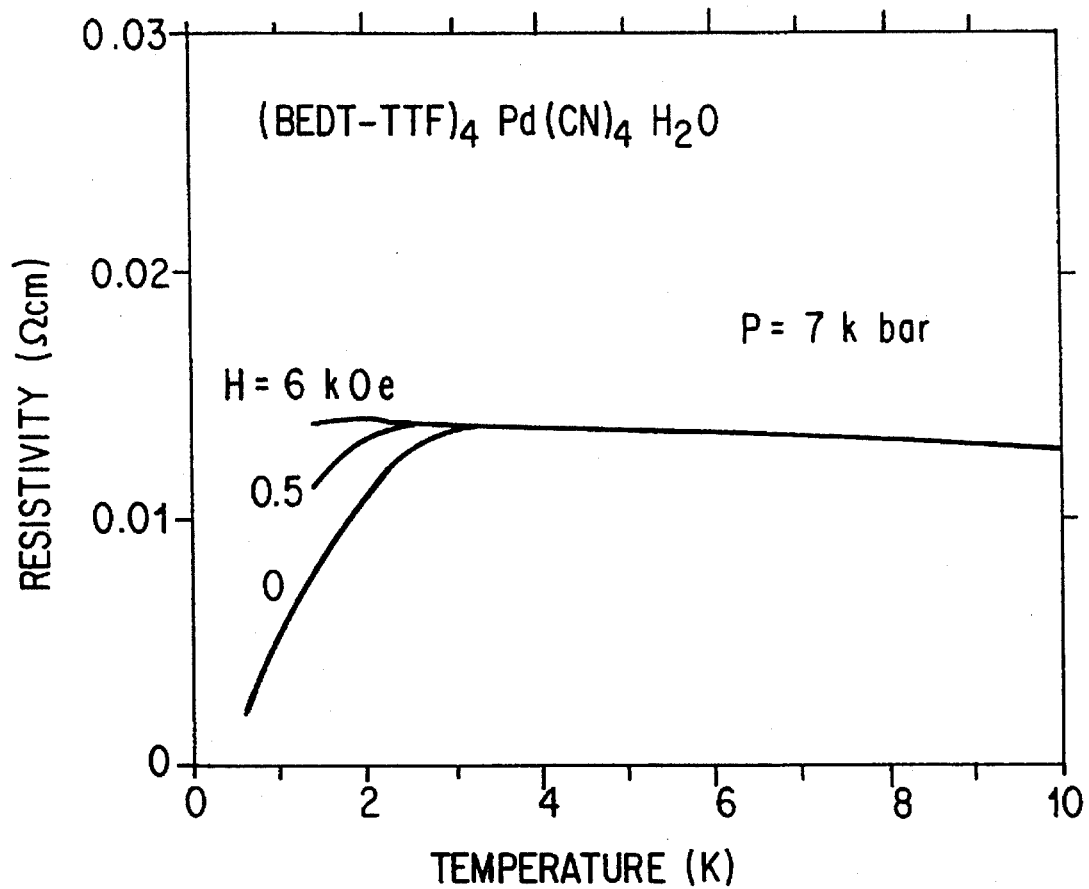
FIG. 19 is the plot showing the temperature dependence of the electrical resistance under pressure of the organic substance of the present invention, $(BEDT-TTF)_4[Pd(CN)_4].H_2O$.

Superconducting phenomenon was observed in (BEDT-TFF)$_4$[Pd(CN)$_4$].H$_2$O. These results are shown graphically in FIGS. 18 and 19. When the crystal was cooled under normal pressure, it showed transition from metal to insulator around 100K. However, when the crystal was cooled subjected to a pressure, superconducting transition took place with a critical temperature of 1.2K at a pressure of 7 kbar.

Figure 20:
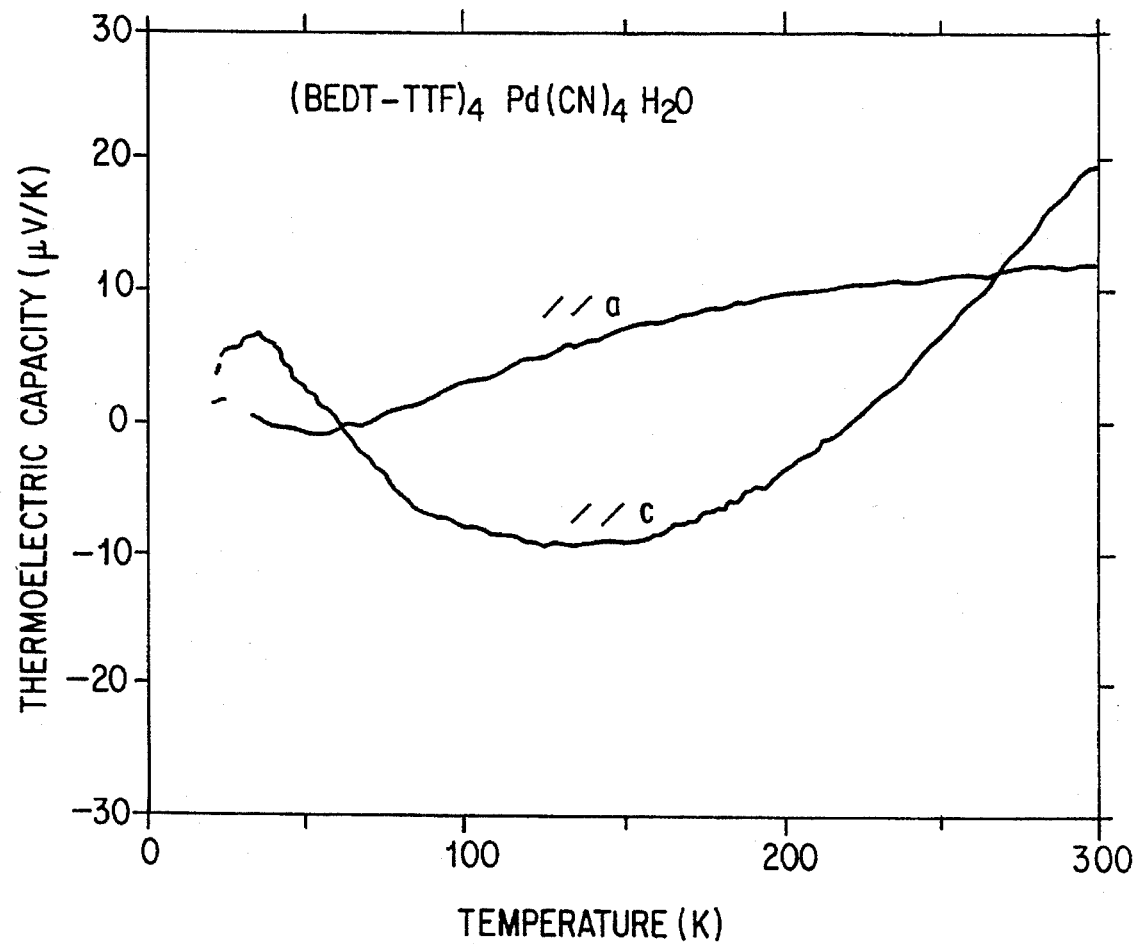
FIG. 20 is the plot showing the temperature dependence of the thermoelectric power of the organic substance of the present invention, $(BEDT-TTF)_4[Pd(CN)_4].H_2O$.

FIG. 20 shows the temperature dependence of thermoelectric power of (BEDT-TTF)$_4$[Pd(CN)$_4$].H$_2$O. The values along the c-axis take up 0 twice at 220K and 60K. This is a consequence of the band structure having a semi-metallic structure, and it shows that the electrical resistance increase at low temperature is not owing to the type of behavior of semi-conductor having a true energy gap.

Figure 21:
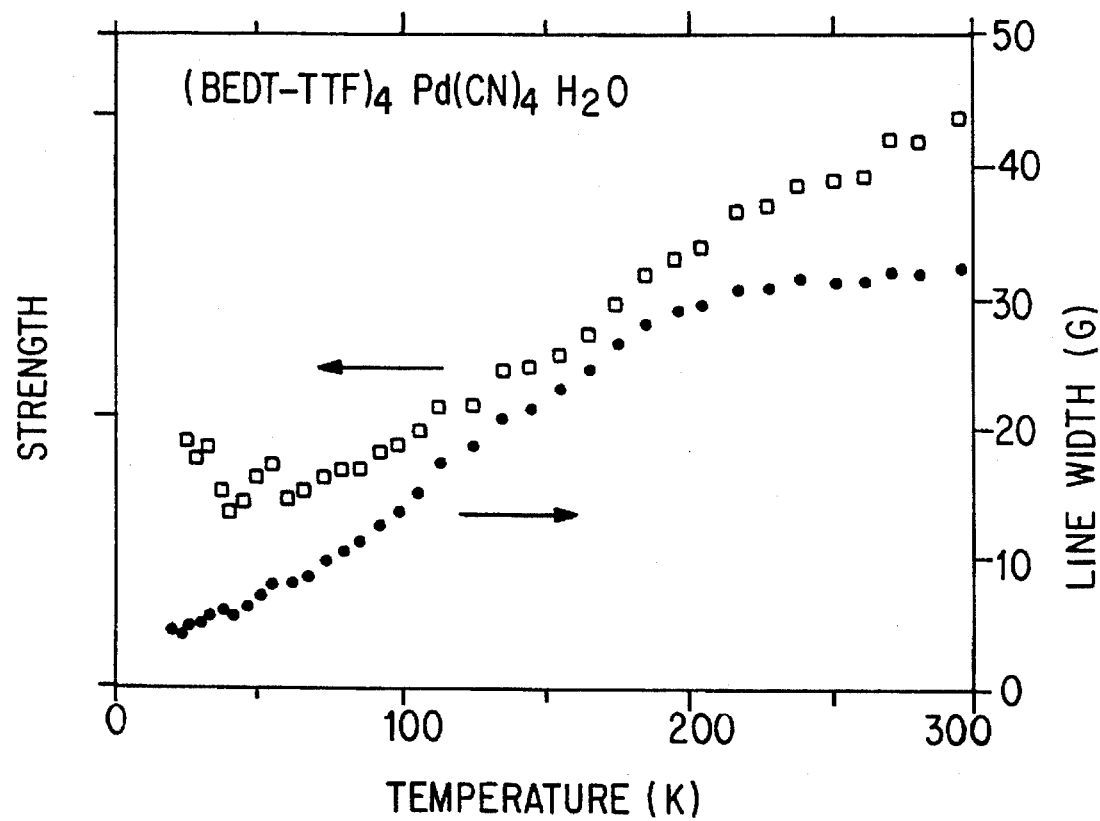
FIG. 21 is the plot showing the temperature dependence of ESR of the organic substance of the present invention, $(BEDT-TFF)_4[Pd(CN)_4·H_2O$.
Figure 22:
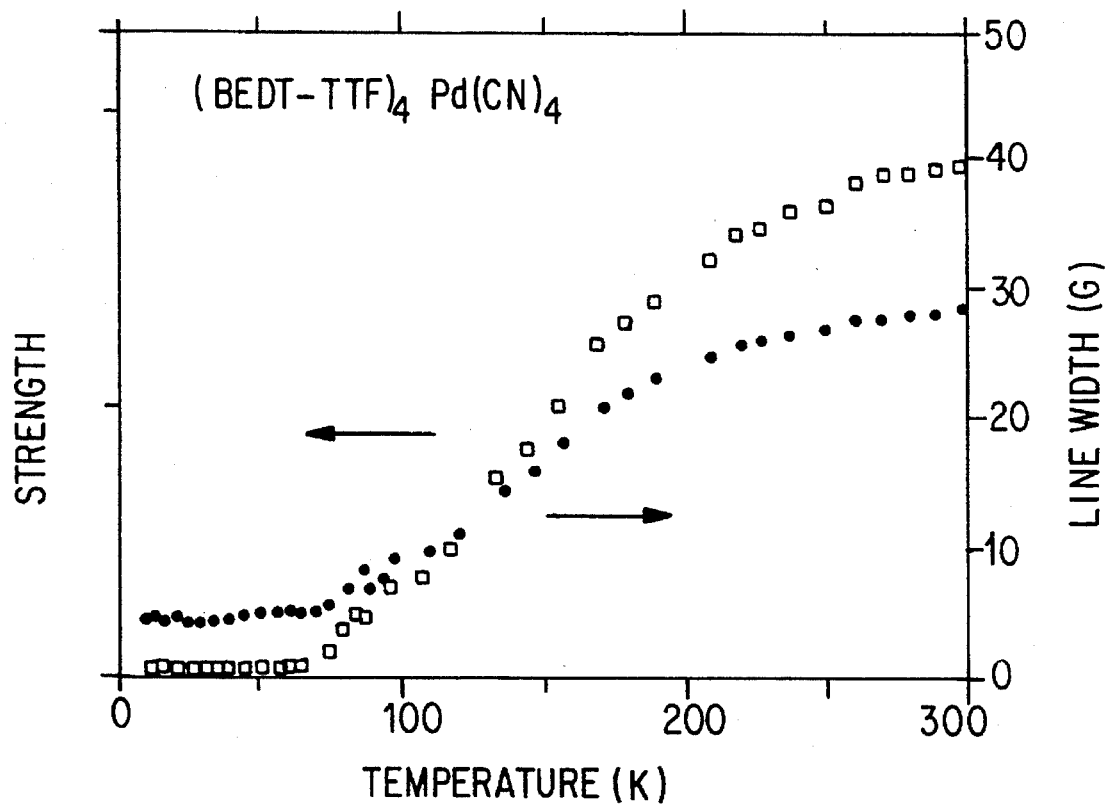
FIG. 22 is the plot showing the temperature dependence of ESR of the organic substance of the present invention, $(BEDT-TTF)_4[Pd(CN)_4]$.

FIGS. 21 and 22 show the temperature dependence of electronic spin resonance (ESR) of (BEDT-TTF)$_4$[Pd(CN)$_4$].H$_2$O and (BEDT-TTF)$_4$[Pd(CN)$_4$]. In contrast to (BEDT-TTF)$_4$[Pd(CN)$_4$] of FIG. 22, which becomes of zero magnetic susceptibility below 70K, the magnetic susceptibility of (BEDT-TTF)$_4$[Pd(CN)$_4$].H$_2$O of FIG. 22 is not zero even at low temperatures showing the fact that carriers are still present. It thus became clear that (BEDT-TTF$_4$[Pd(CN)$_4$].H$_2$O is semi-metallic even at low temperatures compared to (BEDT-TTF)$_4$[Pd(CN)$_4$], which at low temperature is a semi-conductor having a true energy gap.

What is claimed is:

1. Superconductive tetracyano platinum acid bis(ethylene-dithio)tetrathiafulvalene salt.hydrate which is represented by (BEDT-TTF)$_4$[Pt(CN)$_4$].H$_2$O.

2. Superconductive tetracyano palladium acid bis(ethylene-dithio)tetrathiafulvalene salt.hydrate which is represented by (BEDT-TTF)$_4$[Pd(CN)$_4$].H$_2$O.

* * * * *